United States Patent [19]
Paiement et al.

[11] Patent Number: 5,652,954
[45] Date of Patent: Aug. 5, 1997

[54] PIVOTAL EYE PROTECTION SHIELD FOR HEADGEAR

[75] Inventors: Pierre Paiement, St-Jérôme; Christian Pilon, Montreal, both of Canada

[73] Assignee: Itech Sport Products inc., Dollard des Ormeaux, Canada

[21] Appl. No.: 576,226

[22] Filed: Dec. 21, 1995

[51] Int. Cl.⁶ .................................................. A61F 9/02
[52] U.S. Cl. ................................... 2/10; 2/452; 2/453
[58] Field of Search ........................... 2/15, 10, 9, 452, 2/453, 8

[56] References Cited

U.S. PATENT DOCUMENTS

| | | | |
|---|---|---|---|
| 2,502,162 | 3/1950 | Malcom | 2/453 |
| 2,588,553 | 3/1952 | McWathy | 2/453 |
| 3,553,734 | 1/1971 | Aileo | 2/10 |
| 4,312,078 | 1/1982 | Pollitt et al. | 2/10 |
| 4,726,074 | 2/1988 | Baclit et al. | 2/10 |
| 5,012,528 | 5/1991 | Pernicka et al. | 2/10 |
| 5,105,475 | 4/1992 | Lynd et al. | 2/10 |
| 5,357,292 | 10/1994 | Wiedner | 2/453 |
| 5,373,583 | 12/1994 | Birum | 2/10 |

FOREIGN PATENT DOCUMENTS 995665  6/1965  United Kingdom .......................... 2/10

*Primary Examiner*—Michael A. Neas
*Attorney, Agent, or Firm*—Swabey Ogilvy Renault; Guy J. Houle

[57] ABSTRACT

An eye protection transparent shield for use with a headgear. The shield comprises a visor of transparent material and having opposed side connecting portions for pivotal securement to the headgear. The visor has an eye viewing portion and a nose support piece. A pivotal locking mechanism attaches each of the opposed side connecting portions to the headgear. The pivotal locking mechanism has a pivot connection and a guide mechanism for displacing the visor from a position of use, in front of the wearer's eyes, to a position of non-use above the wearer's eyes. The visor is arrested at both positions by a resiliently biased element which also applies a continuous retention force.

14 Claims, 2 Drawing Sheets

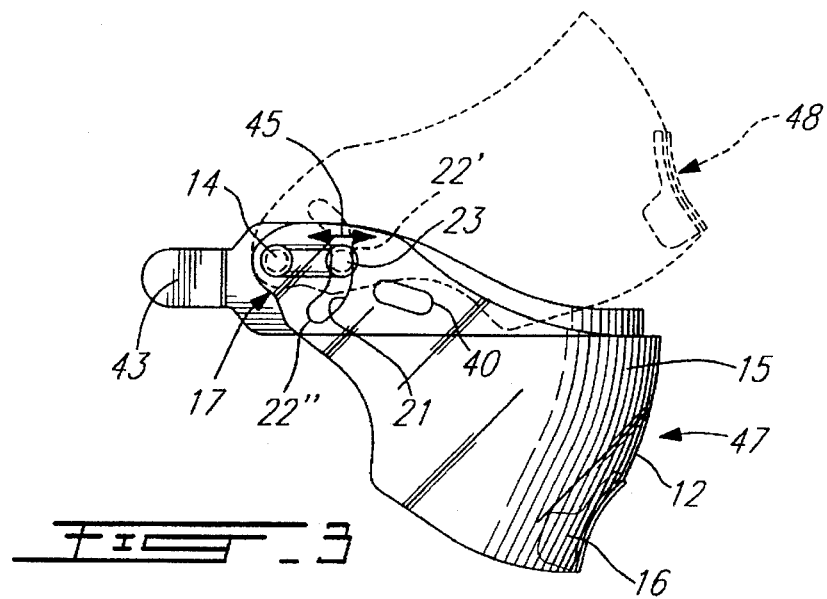
FIG_3
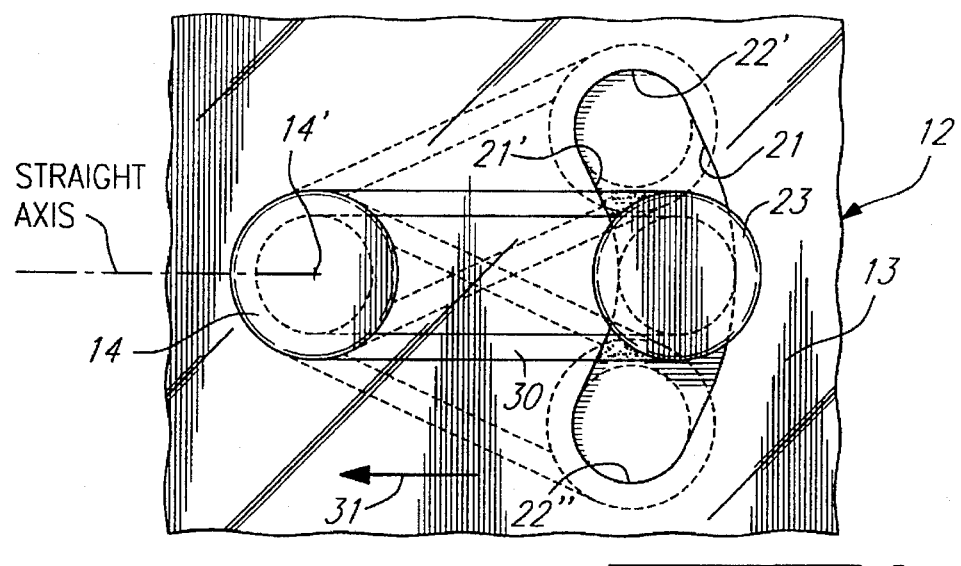
FIG_4
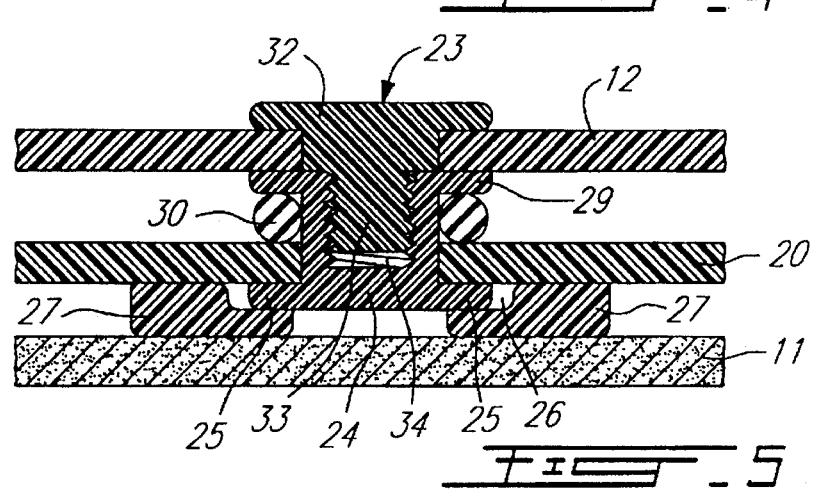
FIG_5

5,652,954

PIVOTAL EYE PROTECTION SHIELD FOR HEADGEAR

TECHNICAL FIELD

The present invention relates to an eye protection transparent shield which is provided with a pivotal locking mechanism to hold the eye shield at a position of use in front of the wearer's eyes, and a position of non-use away from the wearer's eyes.

BACKGROUND ART

It is known to pivotally secure an eye shield or eyeglasses to a headband as, for example, described in U.S. Pat. Nos. 4,885,808 and 5,105,475. Some of the disadvantages of these eye protection devices, securable to headband or other form of headgear, is that these are not secured in a very rigid manner and when subjected to impact they break or disconnect and can sometimes injure the user. These eyeglasses or eye shields are not rigidly retained whilst in a position of use or in a position of non-use. Furthermore, these eye shields are not adjustable with respect to their forward spacing in front of the wearer's eyes whereby to accommodate users having different facial characteristics. Still further, when such devices are damaged it is difficult, if not impossible, to repair.

SUMMARY OF THE INVENTION

It is therefore a feature of the present invention to provide an eye protection transparent shield for use in combination with a headgear and which substantially overcomes the above disadvantages of the prior art.

Another feature of the present invention is to provide an eye protection transparent shield for use in combination with a headgear and wherein the shield may be adjusted in a forward direction in front of the wearer's eyes.

Another feature of the present invention is to provide an eye protection transparent shield for use in combination with a headgear and which is easily assembled and disassembled from the headgear.

Another feature of the present invention is to provide an eye protection transparent shield for use in combination with a headgear and comprising a novel pivotal locking mechanism to retain the eye shield in a position of use, in front of the wearer's eyes, and a position of non-use away from the wearer's eyes.

According to the above features, from broad aspect, the present invention provides an eye protection transparent shield in combination with a headgear. The shield comprises a visor of transparent material and having opposed side connecting portions for pivotal securement to the headgear. The visor has an eye viewing portion and a nose support piece. The pivotal locking mechanism attaches each of the opposed side connecting portions to the headgear. The pivotal locking mechanism has a pivot connection and guide means for displacing the visor from a position of use, in front of the wearer's eyes to a position of non-use, above the wearer's eyes. Arresting means maintains the visor at the position of use and non-use while providing a continous retention force.

BRIEF DESCRIPTION OF DRAWINGS

A preferred embodiment of the present invention will now be described with reference to the accompanying drawings in which:

FIG. 3 is a side view showing the shield at its position of use and non-use and the pivotal locking mechanism;

FIG. 4 is an enlarged view showing the arcuate slot and the travel of the visor with respect to the resiliently biased slot engaging post; and FIG. 5 is a fragmented side view showing the construction of the resiliently biased slot engaging member and its relation with respect to the headband, the visor attaching member and the visor side connecting portion.

DESCRIPTION OF PREFERRED EMBODIMENTS

Figure 1:
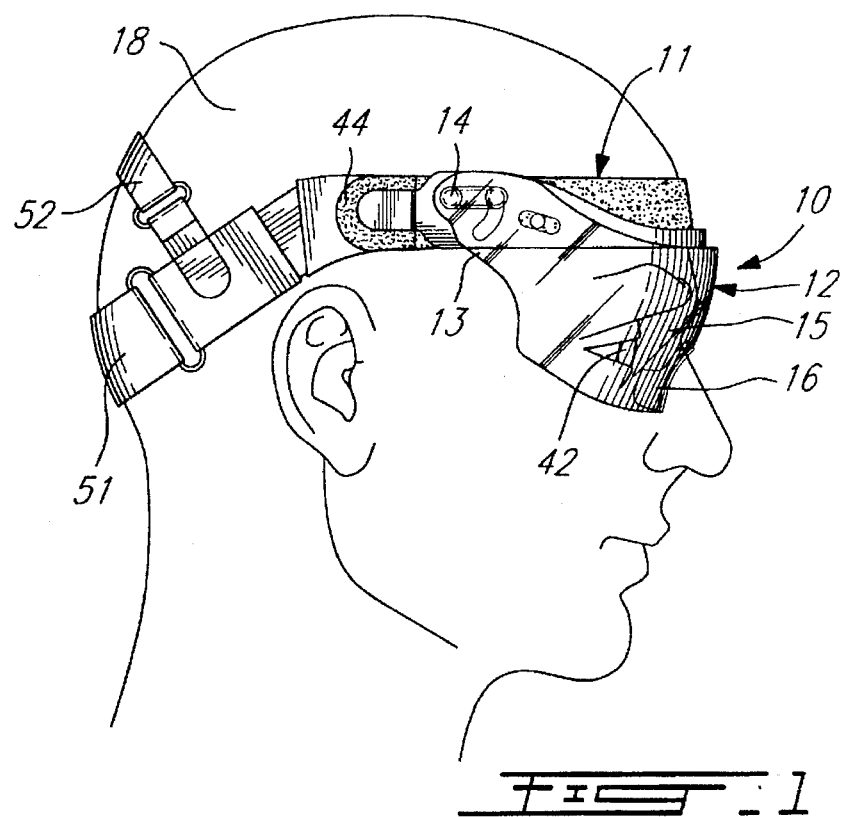
FIG. 1 is a side view showing a wearer person adapted with the eye protection transparent shield/headgear combination of the present invention.

Referring now to the drawings there is shown generally at 10 the eye protection transparent shield of the present invention in combination with a headgear, herein in the form of a sweatband 11. The shield comprises a visor 12 herein formed of transparent plastic material and defining opposed side connecting portions 13 having a hole 19 for pivotal connection to the headgear by receiving on the pivot post 14 provided on each side of the sweatband 11 therethrough. A flanged end nut (not shown) connects to the top of the post 14 to retain the visor. The visor 12 also defines an eye viewing portion 15 and has a nose support piece 16.

Figure 2:
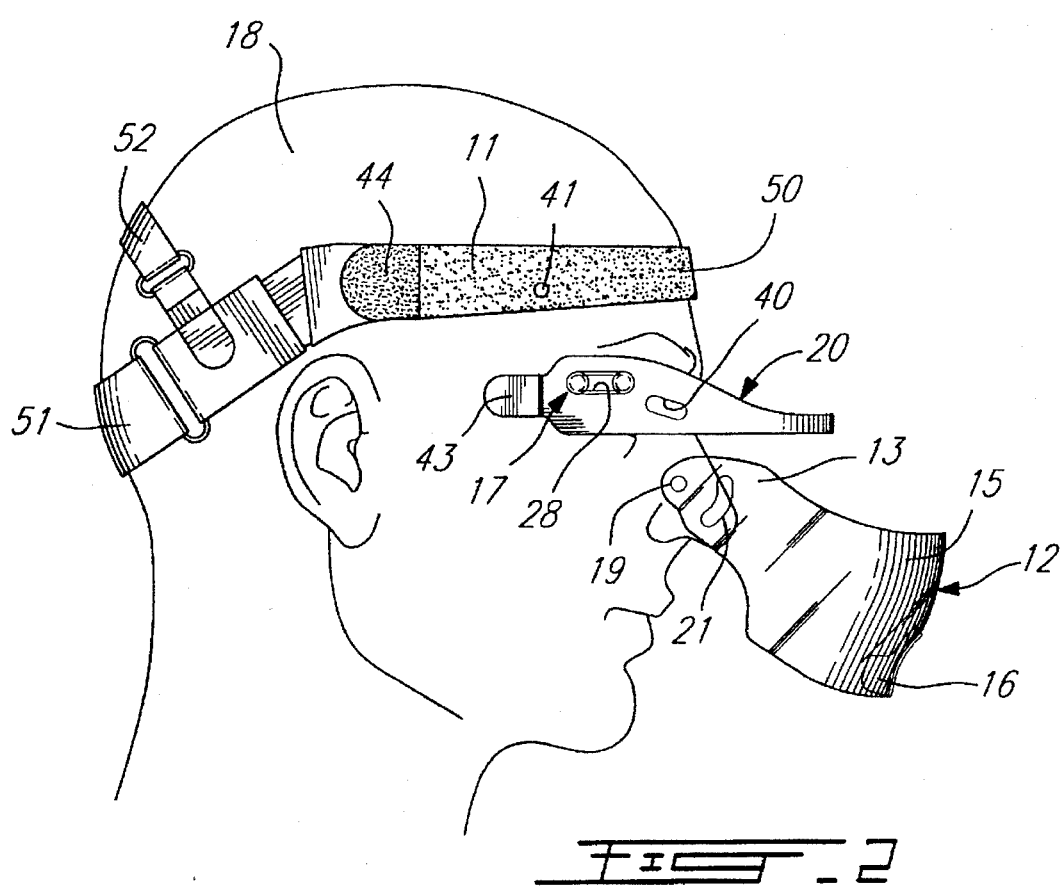
FIG. 2 is a view similar to FIG. 1 but showing the eye protection shield in an exploded unassembled state.

The visor 12 is pivotally connected to the sweatband by a pivotal locking mechanism 17 as illustrated in FIGS. 2 and 3 whereby to attach each of the opposed side connecting portions 13 of the visor to the headband. It is pointed out that the headgear could also be in the form of a cap, visor or helmet or other suitable form of headgear fitted on the wearer's head 18.

As better seen in FIGS. 3 and 4, the pivotal locking mechanism has a pivot connection formed by the pivot post 14 which is secured to the headband or a headgear (not shown) and as shown in this preferred embodiment, it is secured to a visor attaching member 20, as will be described in detail later on. The pivot connection 17 also has a guide means in the form of a curved slot, herein an arcuate slot 21 disposed at a predetermined distance with respect to the pivot post 14 and extends on an arc from the center 14' of the pivot post. The slot 21 has opposed terminal ends 22 which have a curved shape whereby to accommodate resiliently biased slot engaging member or post 23. The curved slot need not be disposed on an arc and could have a different curved shape.

As shown in FIG. 5 the resiliently biased slot engaging post 23 has a base 24 having shoulder portions 25 held captive within a guide channel 26 formed by opposed channel members 27 secured to the underside of the visor attaching member 20. A slot 28 is formed in the visor attaching member 20 to permit axial displacement of the slot engaging post 23 along a straight axis towards the pivot post 14. This slot 28 may be a very short slot to permit this movement. An elastic loop or band 30 is disposed about the slot engaging post 23 and the pivot post 14 and applies a pulling force on the post 23 in the direction of arrow 31, as shown in FIG. 4 so that a continuous retention or pulling force applied against the inner edge 21' of the slot 21. As herein shown, the elastic loop 30 is disposed under the visor 12 but it is conceivable that it could also be disposed above the visor. As also shown in FIG. 5, the base 24 of the slot engaging post 23 has an upper flange wall 29 and a recess threaded bolt 32 dimensioned such that the visor 12 is displaceable along its slot 21 between its terminal ends 22. The bolt 32 has a threaded shaft 33 threadably secured within the threaded bore 34 of the base 24.

Referring more specifically to FIGS. 2 and 3, there will be described the construction of the visor attaching member 20 which is removably secured to the headband or sweatband 11. This visor attaching member 20 is formed of plastic material and has a guide slot 40 disposed at an angle, and spaced from the opposed ends of the band forwardly of the slot 28. An attaching post 41 is secured to the headgear 11 and projects into the guide slot 40 when the visor is assembled on the headband whereby to provide limited displacement of the visor 12 with respect to the wearer's eyes 42. The visor attaching member 20 is also provided with fastening means in the form of Velcro tabs 43 at the terminal ends thereof for matting attachment to a larger Velcro tab 44 secured to the headgear. Accordingly, to adjust the position of the visor with respect to the wearer's eyes, it is necessary to disconnect the Velcro tabs 43 and move the visor towards or away from the wearer's eyes, as shown by arrow 45 in FIG. 3 and then to reconnect the tabs 43 and 44 together at the proper position of the visor. This provides an efficient and simple adjusting mechanism.

As shown in FIGS. 4 and 5, the pivot post as well as the slot engaging post 23 are of circular cross-section. The visor 12 is also molded from clear plastic material and has a certain flexible tolerance whereby to adapt to heads of different widths. The visor attaching member 20 is also formed of flexible plastic material whereby to fit to heads of different sizes and shapes. As shown in FIGS. 3 and 4, when the visor is in its position of use as shown at 47, the slot engaging means which is the post 23 is engaged with the top terminal end 22' of the arcuate slot 21. When in its position of non-use, as shown at 48 the engaging post 23 is at the bottom terminal end 22" of the slot, as illustrated in phantom in FIG. 4. The post is stationary and the visor is displaced. The elastic band 30 has a predetermined tensil force whereby to exert a predetermined pulling force in the direction of arrow 31 when the biasing slot engaging post 23 is at the terminal ends of the slot. The maximum pulling force is, of course, applied at the center of the slot as the visor is being lifted or lowered from its position of use or position of non-use. It can, therefore, be seen that as the visor is lifted or lowered and the post 23 passes the middle portion of the slot, it applies a maximum pulling force on the arcuate inner edge 21' of the slot causing the visor to automatically move to its position of use 47 or position of non-use 48 as it passes this middle portion.

As shown in FIGS. 1 and 2, the headband 11 has a frontal sweatband portion 50 secured to an angulated rear adjustable band 51 and an adjustable rear top band 52.

It is also contemplated that the slot engaging post be biased by other means than an elastic band 30. For example, the post could be molded with the visor attaching member 20 and be connected by an arcuate bridge piece formed with the member 20 and disposed within a slot opening. The bridge piece would apply the retention pulling force on the post back in the direction of arrow 31. Accordingly, this slot engaging post could be formed integral with the attaching member 20 or simply secure to an arcuate bridge piece standing in a slot.

It is within the habit of the present invention to cover any obvious modifications of the preferred embodiment described herein, provided such modifications follow within the scope of the appended claims.

We claim:

1. An eye protection transparent shield in combination with a headgear, said shield comprising a visor of transparent material and having opposed side connecting portions for pivotal securement to said headgear, said visor having an eye viewing portion and a nose support piece, a pivotal locking mechanism attaching each said opposed side connecting portion to said headgear, said pivotal locking mechanism having a pivot connection and guide means for displacing said visor from a position of use in front of a wearer's eyes to a position of non-use above said wearer's eyes, arresting means to maintain said visor at said positions of use and non-use while providing a continuous retention force, said guide means being comprised of a curved slot in said opposed side connecting portions and disposed a predetermined distance from said pivot connection, said slot having opposed terminal ends, a resiliently biased slot engaging member extending through said slot and displaceable along a straight axis transverse to said slot as said visor is displaced between said positions of use and non-use and exerting a pulling force when said slot engaging member is at said terminal ends to retain said visor at said positions of use and non-use.

2. An eye protection transparent shield as claimed in claim 1, wherein there is further provided adjustable guide means to displaceably secure said visor at a desired spacing from said wearer's eyes.

3. An eye protection transparent shield as claimed in claim 1, wherein an elastic element is secured to said slot engaging member to provide a constant pulling force towards said pivot connection.

4. An eye protection transparent shield as claimed in claim 3, wherein said pivot connection is a pivot hinge post secured to said headgear and extending through a pivot hole in said visor disposed in said opposed side connecting portion rearwardly of said curved slot, said elastic element being an elastic loop removably secured about said hinge post and said slot engaging member.

5. An eye protection transparent shield as claimed in claim 4, wherein said curved slot is an arcuate curved slot with said hinge post disposed at a center point of said arc.

6. An eye protection transparent shield as claimed in claim 4, wherein said slot engaging member is a retention post having a base which is held slidingly captive in a guide channel secured to said headgear for axial displacement along said straight axis.

7. An eye protection transparent shield as claimed in claim 6, wherein said elastic loop is disposed about said hinge post and said retention post and disposed under said side connecting portion of said visor.

8. An eye protection transparent shield as claimed in claim 4, wherein said hinge post is secured to a visor attaching member which is removably secured to said headgear, said visor attaching member being provided with adjustable guide means to displaceably secure said visor at a desired spacing from said wearer's eyes.

9. An eye protection transparent shield as claimed in claim 8, wherein said visor attaching member is a formed band, a guide slot adjacent opposed ends of said formed band, an attaching post secured to said headgear and projecting into said guide slot to provide limited displacement of said visor with respect to said wearer's eyes, and fastening means at said opposed ends to attach said visor attaching member to said headgear.

10. An eye protection transparent shield as claimed in claim 9, wherein said fastening means is a Velcro tab for connection to a further larger Velcro tab secured to said headgear.

11. An eye protection transparent shield as claimed in claim 10, wherein said headgear is a sweatband.

12. An eye protection transparent shield as claimed in claim 8, wherein said guide channel of said retention post is secured on a rear wall of said visor attaching member with said retention post extending through a straight guide slot extending co-extensively with said guide channel along said straight axis, said retention post having a circular cross-section and a flanged bottom end received captive in said channel on opposed sides of said guide slot.

13. An eye protection transparent shield as claimed in claim 1, wherein said visor is a rigid visor molded from clear plastic material.

14. An eye protection transparent shield as claimed in claim 8, wherein said visor attaching member is a flexible plastic band having opposed securable ends for removable connection to said headgear.

* * * * *